US00PP21007P3

(12) United States Plant Patent
Swartz

(10) Patent No.: US PP21,007 P3
(45) Date of Patent: May 25, 2010

(54) RASPBERRY PLANT NAMED 'MARCIANNA'

(50) Latin Name: *Rubus ideaus*
Varietal Denomination: Marcianna

(75) Inventor: Harry Swartz, Laurel, MD (US)

(73) Assignee: Five Aces Breeding LLC, Laurel, MD (US)

( * ) Notice: Subject to any disclaimer, the term of this patent is extended or adjusted under 35 U.S.C. 154(b) by 188 days.

(21) Appl. No.: 12/290,889

(22) Filed: Dec. 11, 2007

(65) Prior Publication Data

US 2009/0151035 P1 Jun. 11, 2009

(51) Int. Cl.
*A01H 5/00* (2006.01)

(52) U.S. Cl. ..... Plt./204

(58) Field of Classification Search ..... Plt./204
See application file for complete search history.

(56) References Cited

U.S. PATENT DOCUMENTS

PP6,597 P 2/1989 Keep et al.
PP7,067 P 12/1989 Sanford et al.
PP10,411 P 5/1998 Swartz et al.
PP10,412 P 5/1998 Swartz et al.
PP11,418 P 6/2000 McNicol et al.
PP12,173 P2 10/2001 Swartz et al.
PP14,804 P2 5/2004 Fear et al.
PP15,647 P2 3/2005 Swartz et al.
PP17,819 P3 6/2007 Jennings
PP17,986 P3 9/2007 Jennings

*Primary Examiner*—Annette H Para
(74) *Attorney, Agent, or Firm*—Rosenberg, Klein & Lee

(57) ABSTRACT

The present invention is a new and distinct primocane fruiting red raspberry cultivar named 'Marcianna', which is capable of producing large, bright colored, flavorful and firm fruit that has exceptional consumer appeal characteristics. The cultivar is characterized by its leaf pattern change near and after flower initiation on primocanes, its strong and distinctive flavor and firmness and its fruit morphology, specifically its slight imperfections from conic shape. These imperfections include a slight distension and a small bend in its apparent longitudinal axis. 'Marcianna' plants are also unusual in that they produce commercial quantities of large, firm and flavorful fruit in both the fall on primocanes and spring on overwintered floricanes. The floricanes are productive with as little as 250 chilling hours in Spain.

9 Drawing Sheets

Figure 1:
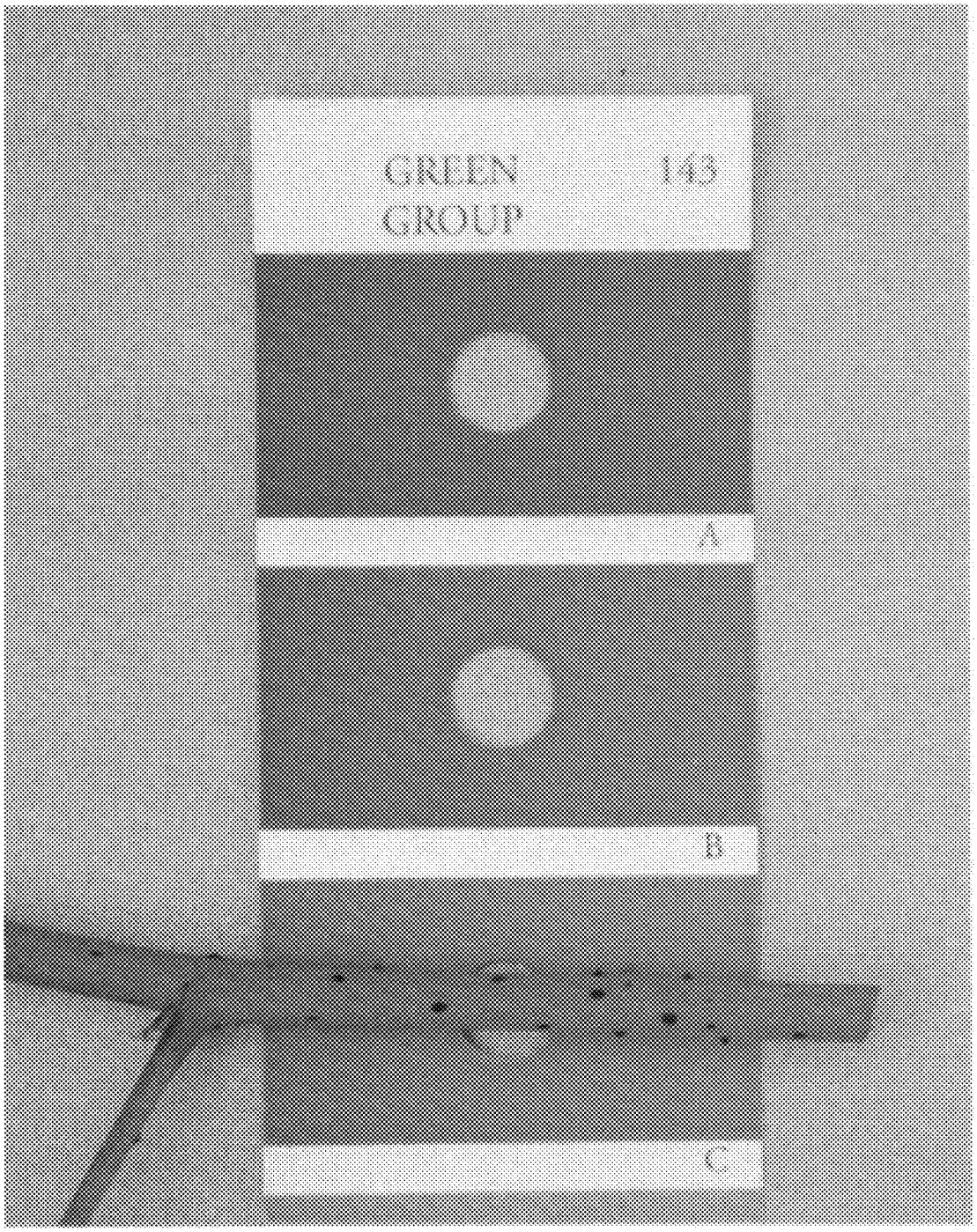

Raspberry plant named 'Marcianna'.

FIELD OF THE INVENTION

This invention concerns a new and distinct cultivar of primocane fruiting raspberry plant with a botanical name of *Rubus ideaus* L. The new cultivar is distinguished from other cultivars by its combination of fruit firmness, sweetness, size, desirable aroma and productivity. '*Marcianna*' is thereby suitable for premium fresh fruit marketing in commercial production areas worldwide.

DESCRIPTION OF RELATED PRIOR ART

Several cultivars of primocane fruiting (commonly known as "fall bearing") raspberry plants are known. For instance, fall bearing raspberry cultivars named 'Anne', 'Caroline', 'Josephine', 'Driscoll Maravilla', 'Jaclyn', 'Marcela' and 'Joan Irene' have been described in U.S. Plant Pat. Nos. 10,411, 10,412, 12,173, 14,804, 15,647, 17,819 and 17,986, respectively. The new and distinct cultivar of the present invention is a raspberry plant named 'Marcianna'. This new and distinct cultivar differs from 'Anne' in bearing red fruit, while 'Anne' bears golden fruit. Compared with 'Anne', 'Marcianna' produces more root and crown-suckers and has significantly higher yield and fruit firmness. 'Marcianna' can be distinguished from 'Caroline' in that '*Marcianna*' fruit is larger, lighter colored, firmer and more cohesive. 'Marcianna' plants produce a lower number of canes than 'Caroline' and yield per plant is therefore lower than 'Caroline'. 'Marcianna' leaves do not regularly curl in high sun and warm temperatures as 'Caroline'. 'Marcianna' also produces a floricane, or overwintered crop of similar size to the primocane crop. 'Caroline' produces smaller sized fruit on floricanes. 'Marcianna' and Josephine are both large fruited primocane fruiting red raspberry cultivars, but 'Marcianna' can be distinguished from 'Josephine' in that 'Marcianna' fruit is produced on primocanes two weeks before 'Josephine' and 'Marcianna' fruit is more conic, sweeter, less pubescent and lighter colored when fully ripe, compared to the round, darker colored, 'Josephine' fruit. 'Marcianna' can be distinguished from 'Driscoll Maravilla' in having more conic, slightly darker red color, slightly softer, sweeter and more cohesive fruit. 'Marcianna' plants are less upright and vigorous with thinner cane diameter and produce fruit two weeks earlier on primocanes than 'Driscoll Maravilla'. 'Marcianna' can be distinguished from 'Jaclyn' in that the fruit ripen on primocanes two to three weeks later than 'Jaclyn', and 'Marcianna' fruit is larger, firmer, sweeter, much lighter colored and easier to remove from the plant. 'Marcianna' can be distinguished from 'Polka' (unpatented) in having larger fruit of similar firmness. 'Marcianna' fruit ripens two weeks later than 'Polka' on primocanes. 'Marcianna' fruit is much sweeter than 'Polka'. 'Marcianna' can be distinguished from 'Marcela' in that 'Marcianna' fruit is more conic, cohesive, larger and flavorful. 'Marcianna' plants are also more vigorous in warmer conditions. 'Marcianna' differs from 'Joan Irene' in that 'Marcianna' fruit are more highly flavored and fruit size is larger and less regular than 'Joan Irene'. 'Marcianna' produces a large floricane crop of the same fruit the size as primocane fruit. Both 'Marcela' and 'Joan Irene' have less productive floricane crops and smaller floricane fruit.

ORIGIN OF THE NEW CULTIVAR

The new cultivar of fall bearing red raspberry originated from a controlled cross at rented glasshouse facilities in College Park, Md. The cross, designated: "CA", was 'Tulameen' (unpatented) ×'Jaclyn' (U.S. Plant Pat. No. 15,647) and was made in the winter of 2002. 'Tulameen' is a premium floricane fruiting red raspberry cultivar with several desirable fruit quality attributes, including flavor, fruit size and reasonable fruit firmness. 'Jaclyn' also has several desirable fruit attributes, such as sunscald resistance and uniformity of fruit size, but is a very early producing primocane type. The cross was made to produce a primocane type with 'Tulameen' fruit quality. 'Jaclyn', tested as "QEG-fl", is a cross of OBC-fl (unpatented) ×'Caroline' (U.S. Plant Pat. No. 10,412). OBC-fl is a selection from the cross KP-2×KAS-1. KP-2 (unpatented) is from a cross of CFO-1×GEN-1. CFO-1 (unpatented) is a cross of 'Southland' (unpatented) ×'Willamette' (unpatented). GEN-1 (unpatented) is a cross of an F2 of *R. pileatus*× SCRI 8216B6 (unpatented). KAS-1 (unpatented) is a cross of GDF-3 (unpatented) ×*R. stellarcticus* 'Linda' (unpatented). GDF-3 is a cross of selection SCRI 52B6 black-purple raspberry (unpatented) ×'Autumn Bliss' (U.S. Plant Pat. No. 6,597). This year of crossing was designated "W". The seed from this cross was exported to the United Kingdom, germinated and grown at Sandbanks Farm, Faversham, Kent United Kingdom. The present invention was second seedling of the WCA progeny selected at Sandbanks in September 2005 and was therefore designated "-v2". Thus, the complete breeding designation of 'Marcianna' is "WCA-v2". The synonyms for "WCA-v2" in Europe are: 'Debonair', 'Royal Scarlet', 'T-Plus', 'Tulameen Plus' and 'Red Jewel'.

SUMMARY OF THE NEW CULTIVAR

This application relates to a new and distinct red fruited, primocane fruiting, raspberry cultivar, botanically known as *Rubus ideaus* L. The following characteristics are outstanding:

1. Production of fruit which is very firm, flavorful, light colored and large.
2. In all the areas of test of this selection, the fruit is larger than all primocane bearing cultivars known to us, except 'Josephine' from the University of Maryland cooperative breeding program.
3. 'Marcianna' canes are more productive than primocane fruiting cultivars tested in the United Kingdom except 'Caroline', 'Joan Squire' (unpatented) and 'Polka' (unpatented). 'Caroline' fruit size is smaller, especially when grown in warmer regions. 'Joan Squire' is softer and less cohesive and 'Polka' has smaller fruit that is much less flavorful.

These characteristics make 'Marcianna' suitable as a late summer primocane fruiting type for premium fresh fruit marketing in commercial production areas worldwide. In cooler areas with less than 2500 growing degree days (base 50 F), 'Marcianna' primocane fruit ripens in mid-August and through September, making it sufficiently early to use as a primocane bearer for almost all agricultural regions in the United States.

Overwintered 'Marcianna' plants with floricanes in southern Spain produced sufficient, but sporadic bud break after mechanical defoliation and 250 chilling hours. This 50-60% bud break response is typical of a genotype which requires a low to moderate (250 to 500) amount of chilling hours. 'Marcianna' plants with floricanes, grown in pots and chilled beginning in early fall, produce sufficient quantities of large, firm and highly flavored fruit to be useful as a primocane and floricane cropping cultivar. Floricane fruit production has not been tested in areas that experience more chilling and significant sub freezing temperatures, therefore, no claims are made concerning cold hardiness below −5 ° C.

The following characteristics are useful in distinguishing this cultivar from other cultivars and can be useful for cultivar identification. Plants used for these observations were grown in uncrowded conditions and in full sunlight.

1. When cane density is below 6 canes per meter of row on non-tissue culture propagated plants at least two years old, 'Marcianna' plants produce primocanes which terminate in flower clusters. 'Marcianna' canes usually produce flowers at the $24^{th}$ node in the United Kingdom. By comparison, 'Jaclyn', 'Caroline' and 'Heritage' (unpatented) produce fruit, on average, at the $15^{th}$, $25^{th}$ and $29^{th}$ nodes, respectively. Above the $24^{th}$ node, an additional 16 nodes produce flower trusses; therefore, 40% of an average, well illuminated, 'Marcianna' primocane produces flowers. 'Marcianna' primocanes will have delayed flowering if overfertilized or grown in shaded conditions.
2. The initial or primary fruit is long conic; on average, 40% longer than wide. Round type fruit, for example: 'Josephine', 'Polka' and 'Driscoll Maravilla', have primary fruit with a ratio of width to length within 10% of 1 to 1. Primary 'Marcianna' fruit have a large receptacle cavity comprising 50% of the diameter the fruit width. This is at least 10% greater than other primocane varieties produced with similar germplasm. There is a slight irregularity to the fruit shape which is characteristic of 'Marcianna'. The fruit receptacle is slightly globular at its base, causing a slight distension of the fruit at the midpoint of its longitudinal axis. This results in an apparent angle between the apparent axis of the top and that of the bottom of the fruit of around 5°. Drupelets are more tightly adhered to each other than 'Driscoll Maravilla' and 'Joan Squire' , but will normally not tear in half before separating from the neighboring drupelets as 'Josephine' or 'Anne'. Upon full ripening, a few drupelets may develop a slight darker coloration under the attachment of the remnant pistil.
3. Thorns are moderately numerous and found in slightly greater abundance on the base of the plant as typical of the species. The coloration of the thorns on primocanes is typical of 'Marcianna' and can be used to distinguish 'Marcianna' from some other cultivars. Thorn coloration is consistently deep grayed purple (Royal Horticultural Society Colour Plate 183A) and the coloration extends about 1 mm. in an oval into the surrounding cane. Thorns are generally 1 mm. in length, relatively thin and slightly downward pointed.
4. Primocanes, petioles and leaf veins are light green (Royal Horticultural Society Colour Plate No 143C) with a slight red blush (Royal Horticultural Society Colour Plate No 184A) on less than 5% of the cane area. The blush is found on small areas throughout the cane and occasionally on the ridges of the interveinal areas of the leaf blades. When plants are at least two years old and grown in non-crowded conditions with adequate nitrogen fertilization and irrigation, leaves are primarily pentafoliolate at the base of the primocane, but are mostly trifoliolate when the transition to fall fruiting leaves occurs. The color of the underside of trifoliolate leaves (Royal Horticultural Society Colour Plate No. 190A) is slightly lighter than the underside of pentafoliolate leaves (Royal Horticultural Society Colour Plate No. 191A). The upper surface color is similar however (Royal Horticultural Society Colour Plate No. 147A).

BRIEF DESCRIPTION OF THE PHOTOGRAPHS

The accompanying photographs show typical characteristics of the new variety:

FIG. 1. shows a 'Marcianna' primocane section with Royal Horticultural Society Colour Plate No. 143.

Figure 2:
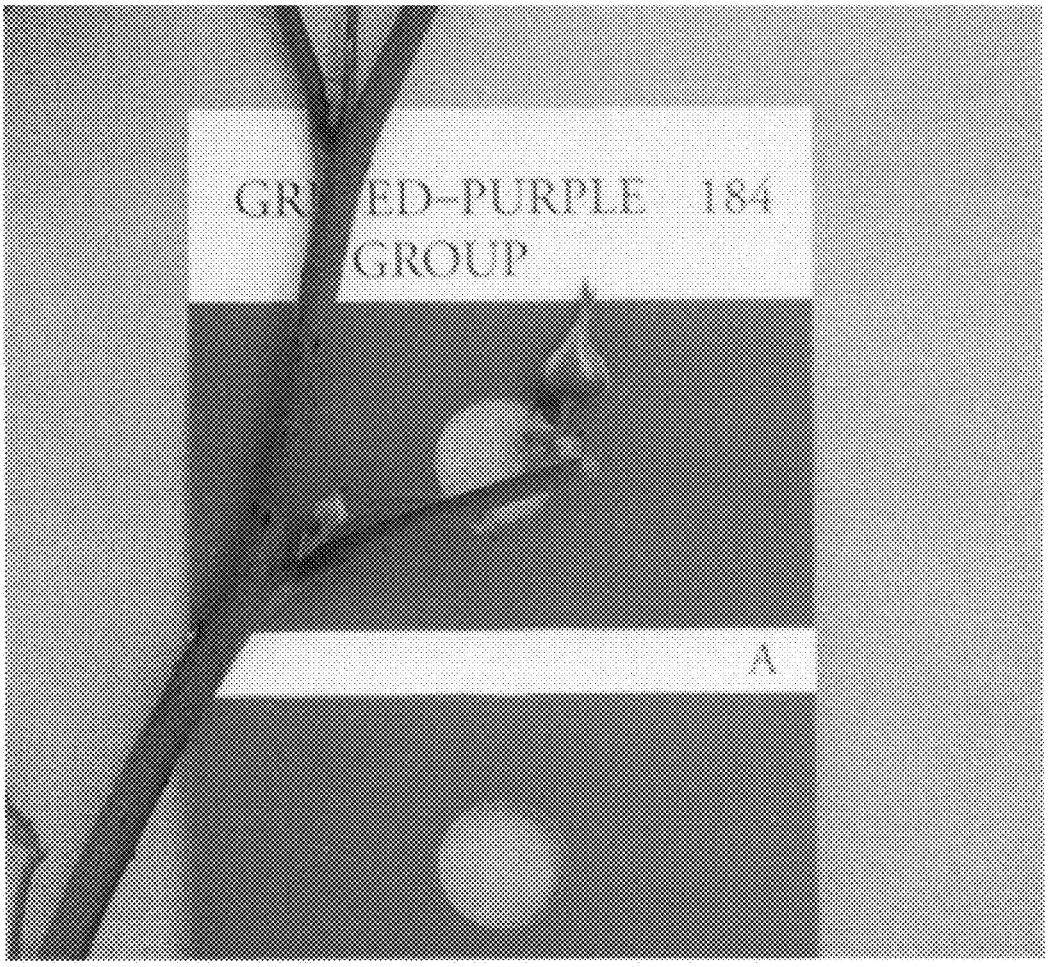

FIG. 2. shows the red blush on a flowering truss of a 'Marcianna' primocane with Royal Horticultural Society Colour Plate 184.

Figure 3:
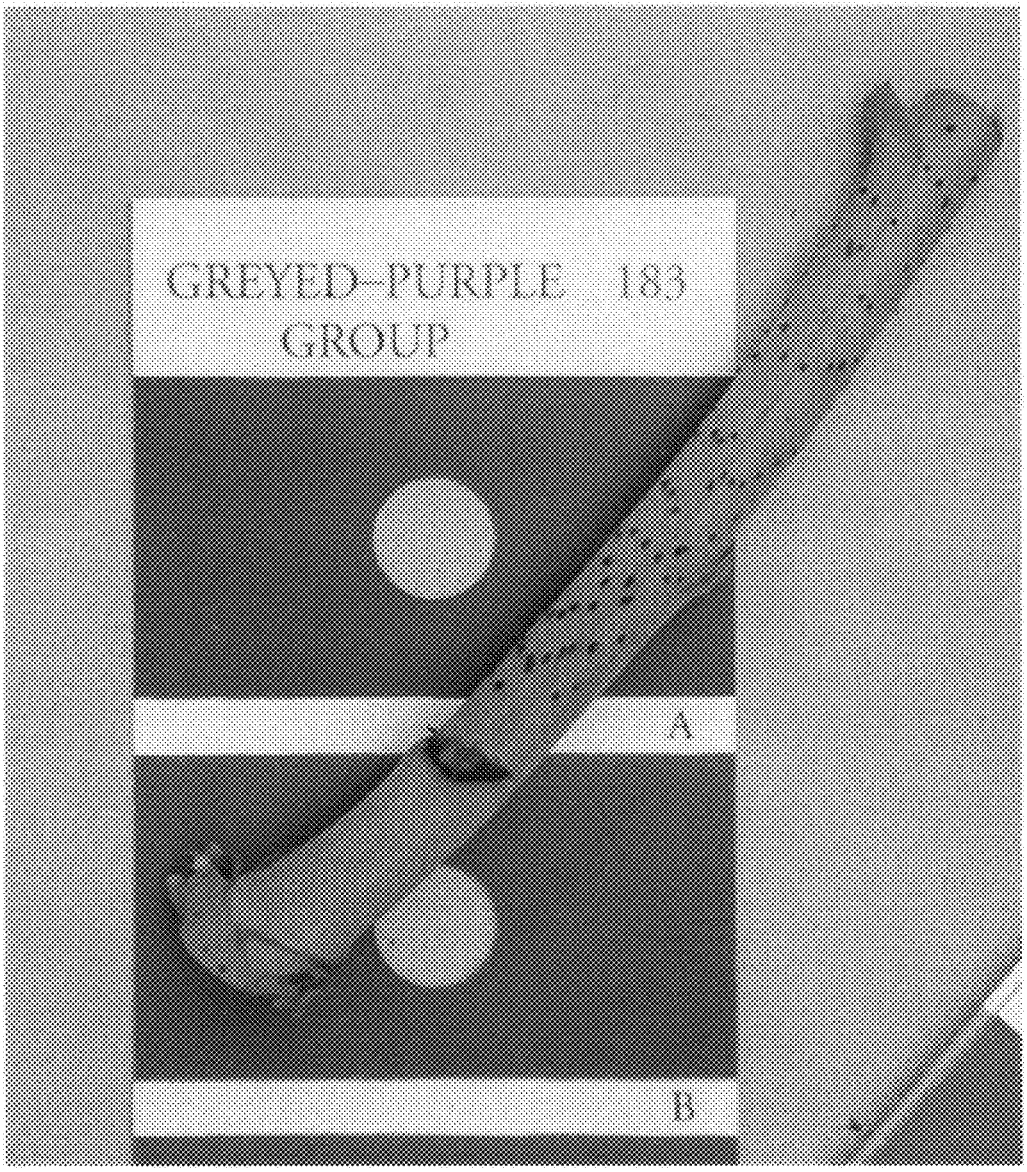

FIG. 3. shows the color, shape and density of thorns on a 'Marcianna' primocane and Royal Horticultural Society Colour Plate No. 183.

Figure 4:
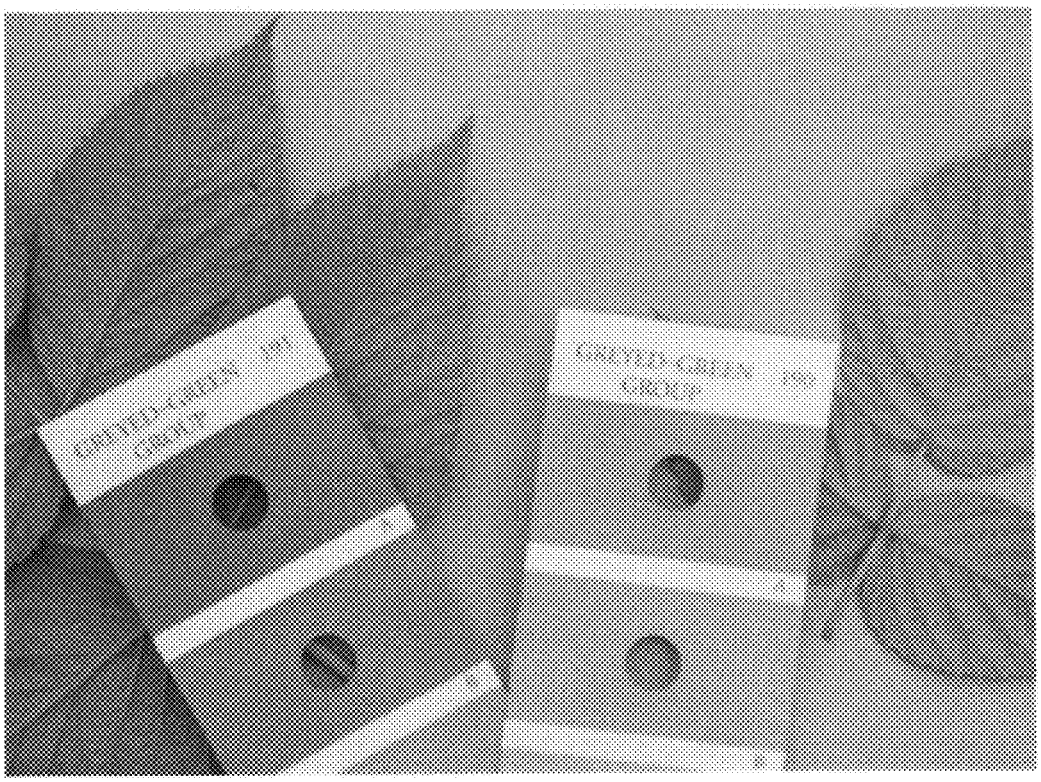

FIG. 4. shows the underside of pentafoliolate and trifoliolate 'Marcianna' leaves and Royal Horticultural Society Colour Plates Nos. 190 and 191.

Figure 5:
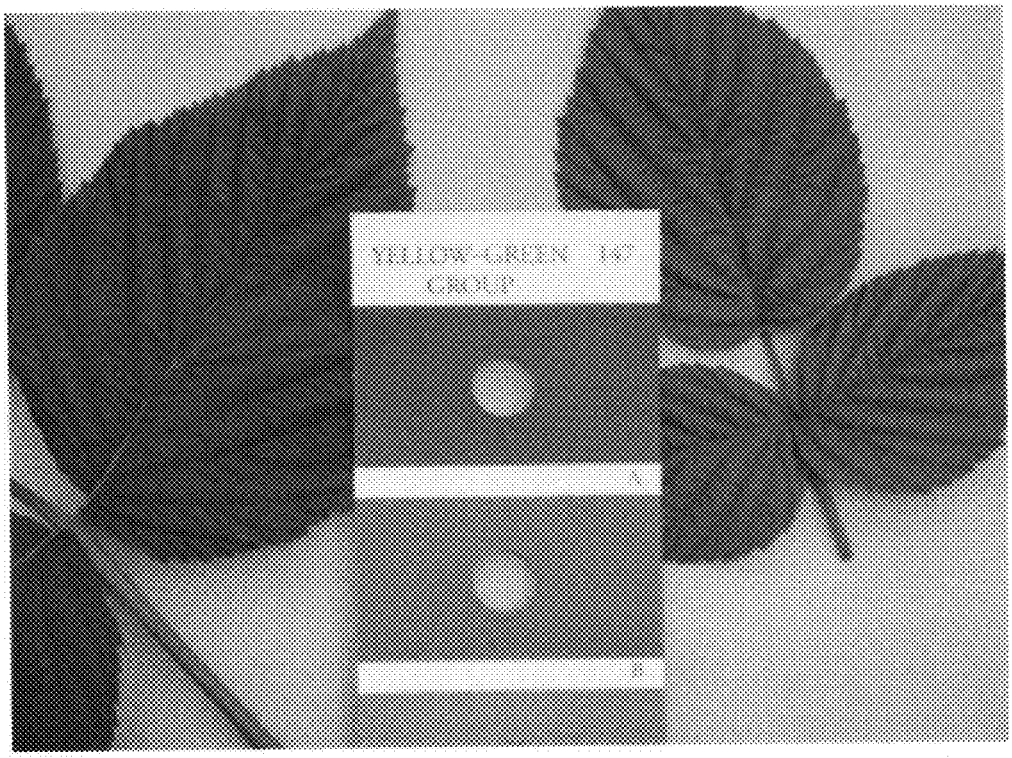

FIG. 5. shows the top surface of a 'Marcianna' leaf with Royal Horticultural Society Colour Plate 147 and the pattern of leaf smoothness and vein pattern.

Figure 6:
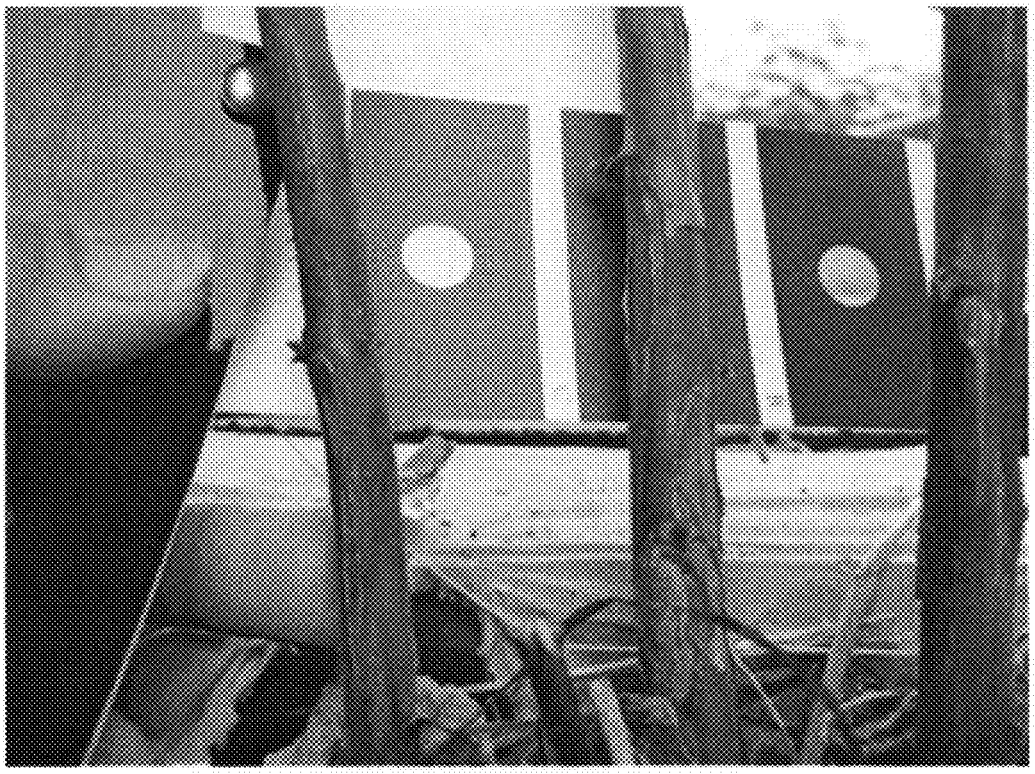

FIG. 6. shows the base of a mature floricane in mid-November and the pattern of slight exfoliation of the bark and Royal Horticultural Society Colour Plate 200.

Figure 7:
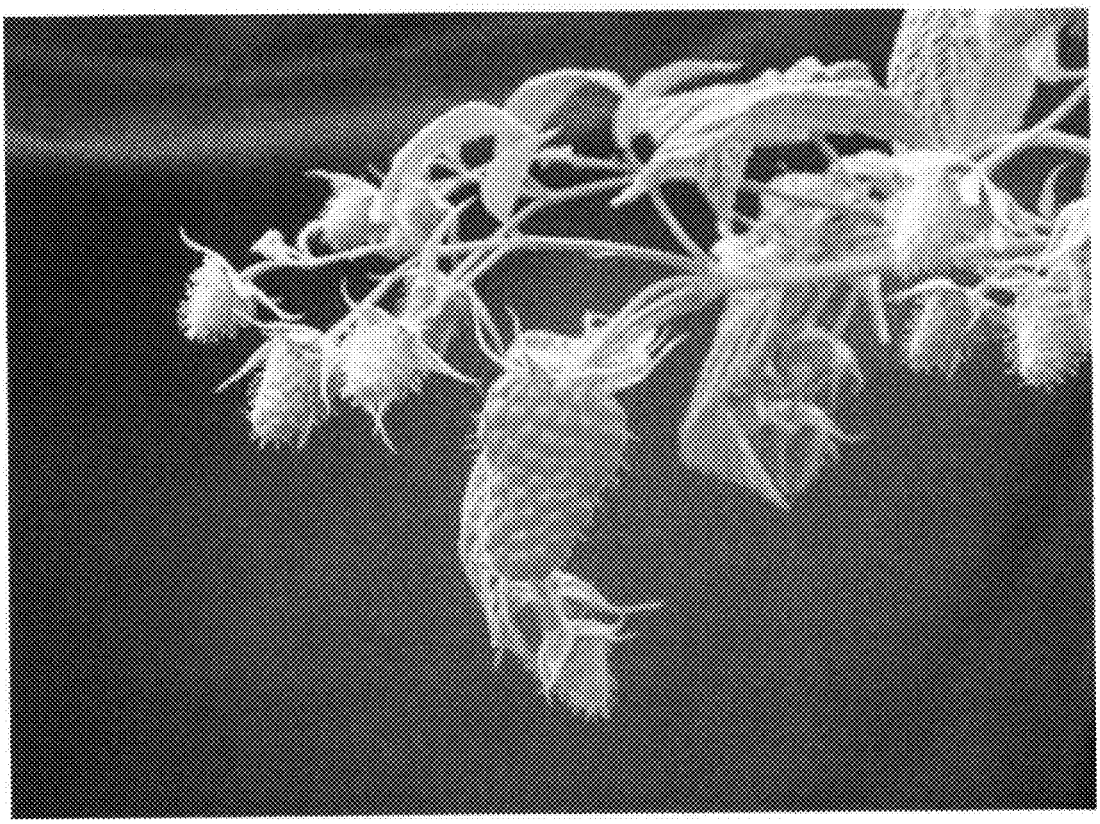

FIG. 7. shows a primocane fruiting cluster of 'Marcianna' in mid August, 2006, showing the exposure of 'Marcianna' fruit as grown in an unheated tunnel.

Figure 8:
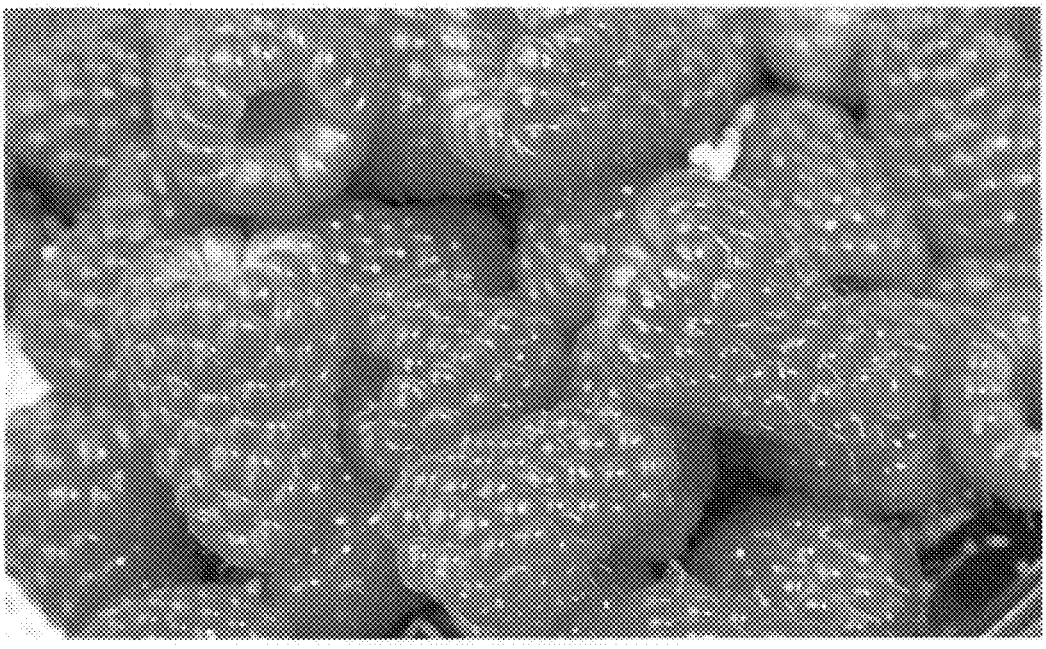

FIG. 8. shows the initial primocane fruit of 'Marcianna' as it would occur in a market.

Figure 9:
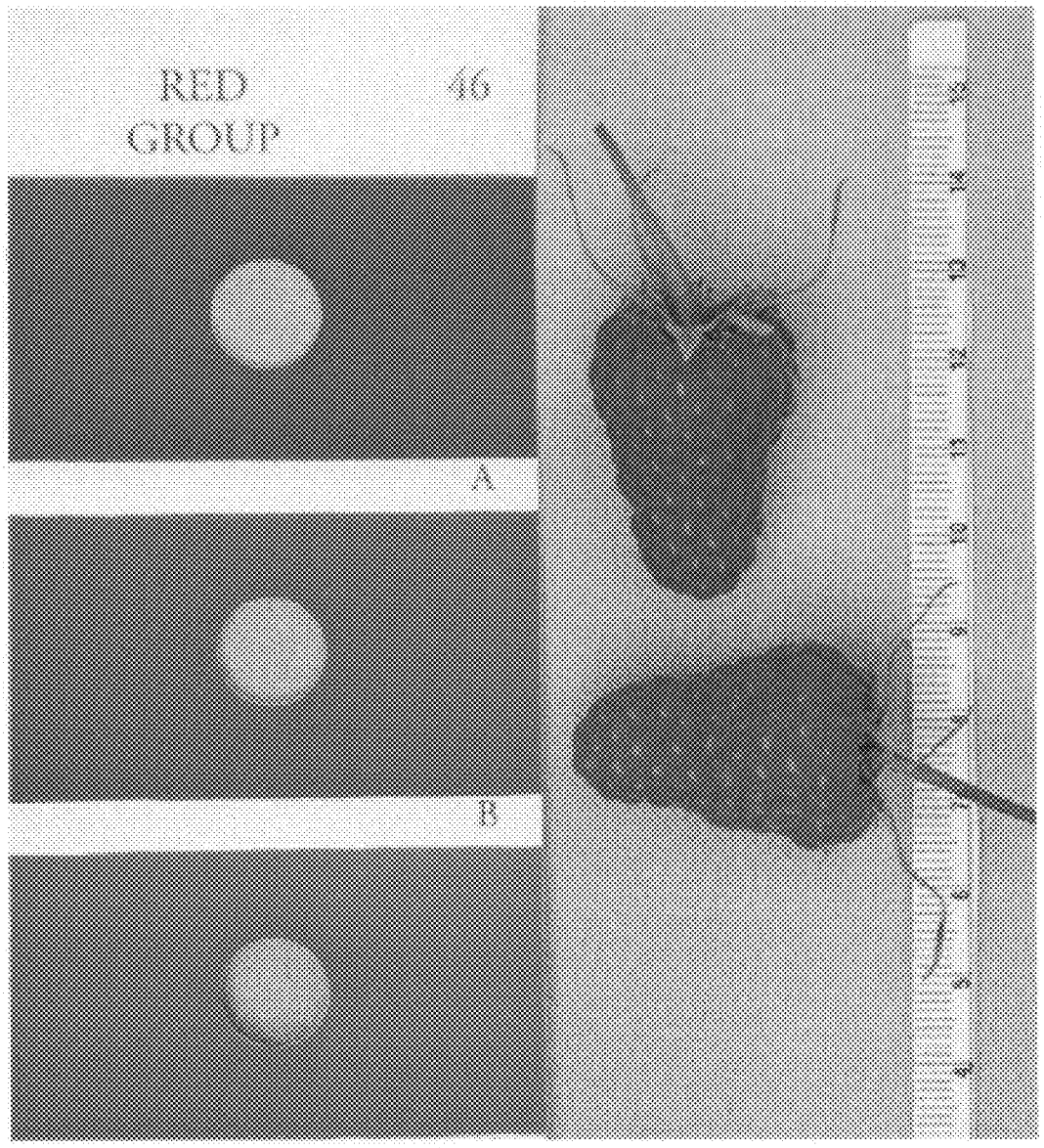

FIG. 9. shows the lighter color of 'Marcianna' fruit and Royal Horticultural Society Colour Plate 46.

DESCRIPTION OF THE NEW CULTIVAR

The following is a detailed description of 'Marcianna', the new cultivar, including fruit production, together with the cultivar's morphological characteristics. 'Marcianna' is a species hybrid, which contains a predominance of *Rubus ideaus* L. traits and would be botanically classified in that species commonly referred to as red raspberries. The characteristics of the cultivar were compared with other standards used in the United Kingdom and Mid-Atlantic Region of the U.S. The description is based on information provided by cooperating growers from plants grown in fields at Faversham, Kent, England, Cartaya, Spain and from plants grown in the greenhouses at College Park, Md. As these climates differ, particularly in temperatures experienced in the growing season, we believe the description of 'Marcianna' will be consistent in other locations. The primocane characteristics described herein were determined on two year old plants grown under high light conditions and adequate fertilization and supplemental irrigation. The floricane characteristics were determined on the same overwintering plants late in the second year and through the third year of growth.

'Marcianna' produces a moderate number of root- and crown-suckers (approximately 6 per foot of row), more than 'Anne' and 'Josephine', but less than 'Caroline' and 'Heritage'. During the growing season, canes are light green colored (Royal Horticultural Society Colour Plate No. 143C) (FIG. 1) with a red blush (Royal Horticultural Society Colour Plate No. 184A) on less than 5% of the cane (FIG. 2). Canes are usually unbranched and erect by the second year of a plant's growth. Total node number per cane is 40 for second year adult, non-tissue culture plants. By comparison, 'Heritage' produces 39 nodes per cane, 'Caroline' produces 36 nodes per cane on tissue culture produced first year plants and 'Josephine' produces 45 to 48 nodes per cane, on older adult or tissue culture produced first year plants. Growth is moderately vigorous, reaching on average 5 feet in full sun, or 7 feet in crowded conditions or in tunnels. Internode length at 30 cm. above ground in well lighted plants without floricanes is 4.75 cm. Cane diameter at the same location was 1.0 cm.

Thorns are moderate in density: ranging from 12 to 90 per internode, with an average of 34 at 30 cm. cane height and an average of 22 at the apex of the cane. Thorn shape is straight and needle-like, (the length of the thorn is greater than four times its diameter) and length is approximately 1 mm (FIG. 3). 'Marcianna' thorn color is grayed purple (Royal Horticultural Society Colour Plate No. 183A) in color throughout; including 1 mm of the surrounding epidermis of the cane. This thorn coloration of the cane is in an oval oriented with the long axis parallel to the axis of the cane. The color of the thorns turns brown in the dormant season, matching that of the overwintering floricanes. A similar pattern occurs with lateral buds, which are typical in size and shape of the species.

The lower surface of trifoliolate 'Marcianna' leaves is pubescent grey-green resembling Royal Horticultural Society Colour Plate No. 190A (FIG. 4). The lower surface of pentafoliolate 'Marcianna' leaves is a slightly darker shade of grey green resembling Royal Horticultural Society Colour Plate No. 191A (FIG. 4). The upper surfaces of both pentafoliolate and trifoliolate leaves are dark green, most closely in hue to Royal Horticultural Society Colour Plate No. 147A, depending on the amount of N fertilization and time of season (FIG. 5). Senescing leaves have a green yellow color resembling Royal Horticultural Society Colour Plate No. 146A. Vigorous plants have leaves that are 90% pentafoliolate at nodes 1 to 18. Above node 22, only trifoliolate leaves occur. The pentafoliolate terminal leaflet is, on average, 7.32 cm. wide and 11.94 cm. long. The trifoliolate terminal leaflet is, on average, 8.42 cm. wide and 11.36 cm. long. The pentafoliolate maximum leaf width, measured from apex of a lateral leaflet to the opposite lateral leaflet apex is, on average, 22.86 cm. The trifoliolate maximum leaf width, measured from apex of the lateral leaflet to the opposite lateral leaflet apex is, on average, 18.52 cm. The pentafoliolate leaf petiole, basal petiolule and apical petiolule lengths averages 7.64 cm, 4.58 cm. and 2.38 cm. respectively for a total of 14.6 cm. The trifoliolate leaf petiole and terminal petiolule lengths averaged 5.08 cm. and 3.08 cm. respectively. Lateral leaflets are sessile and join at the petiole apex with the apical leaf petiolule (FIGS. 4 and 5). Leaf serration, moderate laminar puckering and veination pattern are common for most cultivars of red raspberry and cannot be used to distinguish this cultivar.

Leaves abscise readily in October and November and coloration changes and exfoliation indicative of the change to a floricane occurs in October and November. 'Marcianna' floricanes are blotchy light and moderately dark orange-brown in color, resembling in hue Royal Horticultural Society Colour Plates No. 200B, 200C and 200D for the dark brown patches to Royal Horticultural Society Colour Plate 166A and 166B for the lighter grayed orange brown patches (FIG. 6). Floricanes exfoliate to a moderate amount (FIG. 6).

Flowers appear after 23.8 nodes, on average, on adult plant 'Marcianna' primocanes. By comparison, adult 'Heritage' and 'Josephine' primocanes flower, on average, after 28.5 and 35.8 nodes respectively. Fruit appears on 16.4 nodes on average. Fruit is borne on 40% of the total nodes of the primocanes. The proportion of cane producing fruit is greater than 'Heritage' (unpatented) (27%), 'Caroline' (29%) or 'Josephine' (21%) and, by observation in other fields, this proportion in 'Marcianna' is also greater than that of 'Anne', 'Autumn Bliss' (U.S. Plant Pat. No. 6,597), 'Autumn Britton' (unpatented), 'Amity' (unpatented) or 'Ruby' (U.S. Plant Pat. No. 7,067).

The unscented flower morphology and early fruit morphology is typical of most red raspberry cultivars, having five white (Royal Horticultural Society Colour Plate No. 155D) petals that average 0.59 cm. long, 0.21 cm. wide; petals abscise after pollination. Flowers have five 1.5 to 2.6 cm. long, 0.40 to 0.43 cm. wide at the base triangular grey green sepals (Royal Horticultural Society Colour Plate No. 194B). Sepals are longer on primary fruits. Flowers have on average 81.4 pistils on midseason fruit and a similar number of anthers, 82.6; none of these traits can be used to identify 'Marcianna'. Flower trusses are typical cymose clusters; the total number of flowers is 119.7 on well lighted, uncrowded canes but 45.0 on crowded canes (FIG. 7).

The initial or primary fruit are easily distinguishable by long conic shape for this variety at 12 days post pollination. This larger fruit is long conic with an average sized receptacle cavity about 1.18 cm. diameter. As these fruit are comparatively narrow, 2.31 cm., in diameter the fruit width to receptacle cavity is above average or 50% of the fruit diameter, compared to 30% of the long conic fruited 'Jaclyn' and the round 'Josephine', which has a cavity 40% of the fruit diameter (FIG. 8). The initial mature fruit length was 3.24 cm, producing an initial fruit width to length ratio of 5 to 7, except on smaller fruit where the two dimensions are close to equal. This ratio is similar to 'Jaclyn', a parent, or 'Caroline', a grandparent of 'Marcianna', but longer than 'Josephine', 'Polka' and 'Driscoll Maravilla', which have more nearly round fruit. There is a slight irregularity to the fruit shape which is characteristic of 'Marcianna'. The fruit receptacle is slightly globular at its base, causing a slight distension of the fruit at the midpoint of its longitudinal axis (FIG. 9). This gives a slightly kinked appearance of the fruit when viewed from its side or perpendicular to its central axis. The angle between the apparent axis of the top and that of the bottom of the fruit is around 5° from linear. Early to midseason fruit have 105 drupelets, and average 5.5 grams fresh weight. Later fruit are smaller and average 65 drupelets; this is a relatively small variation in fruit size over the season. 'Marcianna' fruit are cohesive, but, unlike two other large-fruited fall bearing cultivars: 'Josephine' and 'Anne', it will not tear across the drupelets before individual drupelets separate from each other. Unless pollination problems exist, the fruit does not shatter under pressure of hand harvest.

Fruit ripens 25 days after pollination on primocanes in a greenhouse in College Park, Md. Fruit is ripe beginning the first week in August to mid-October in Kent, where the 5% ripe date in 2006 was August 14. In 2007, the 5% ripe date was August 16 and the 50% ripe date was September 3.

'Marcianna' fruit are medium red when ripe, closely resembling the hue of Royal Horticultural Society Colour Plate No. 46A (FIG. 9) and slightly lighter color when underripe, resembling Royal Horticultural Society Colour Plate No. 46B. When fully or over ripe, or upon 7 days storage, fruit develops a darker red color, particularly under the spent pistil. Fruit have a slight amount observable pubescence, typical of most other commercial cultivars, but noticeably less than 'Josephine'. The fruit readily separates from the plant's receptacle in warm conditions, but is slightly more difficult to remove when ripened in colder weather (<55° F.). This is partly due to the long receptacle to fruit interface. The fruit does not break down after at least one week in common storage at 40 ° F. Flavor is sweet and the aroma is strong and characteristic of red raspberry. Spring ripened fruit was rated above 'Tulameen', 'Driscoll Maravilla', and 'Glen Ample' (U.S. Plant Pat. No. 11,418) by a professional taste panel in the United Kingdom. The texture of the fruit is firmer than other eastern US-grown red raspberry cultivars known to us, with the exceptions of 'Josephine', 'Driscoll Maravilla' and 'Polka', all primocane fruiters with similar firmness.

FRUIT PRODUCTION

'Marcianna' has been tested in a replicated trial in Kent and a Sussex glasshouse in the United Kingdom. The following data were collected in the summer and fall of 2006 and 2007. In the Kent test, plants were planted in spring 2005 for the 2006 yield data and again in spring 2006 for the 2007 yield data; the data below could be classified as a normal yield for field production. Total 2006 primocane yield on in ground plants grown in tunnels was 3.1 kg/meter of row for 'Marcianna' and 4.1 kg/meter of row for 'Caroline'. This is from a yield of 1201 g/plant for '*Marcianna*' and 1672 g/plant for 'Caroline'. Total 2007 primocane yield on in ground plants grown in tunnels was 2.8 kg/meter of row for 'Marcianna' and 3.7 kg/meter of row for 'Caroline'. This is from a yield of 1043 g/plant for 'Marcianna' and 1519 g/plant for 'Caroline'. In the Sussex trial, two year old potted '*Marcianna*' plants with 2 or 3 canes per plant and 2 pots per meter produced a floricane crop of 5.3 kg/meter of row when receiving ambient Sussex winter chilling. When similar potted plants were given controlled refrigeration at 4 ° C., yield was 2.3 kg/m after 1344 hours of chilling and 2.0 kg/m after 1092 hours of chill. A yield of 4 kg/m is equivalent to 11,830 lbs/acre at 10 ft between rows. Average fruit weight was 5.5 g on early primocane fruit and 4.7 g on midseason floricane fruit.

The plant is slightly susceptible to late season leaf rust (yellow rust). The plant's reaction to *Phyophthora fragarae* root rot is probably moderately resistant, based on field reaction, not on controlled testing. When plants were excessively watered in pots in a glasshouse, symptoms of *Phytophthora fragarae* were observed. Fruit is usually free from rot in the field, more so than 'Anne' and 'Caroline', but not 'Josephine'.

'Marcianna' has been asexually propagated by tissue culture and by root suckers at the following locations: Faversham, Kent, United Kingdom, College Park, Md., and Burlington, Wash. In each of the aforementioned locations, no off-type plants have been observed in the history of asexual propagation of this cultivar by either method.

What is claimed:

1. A new and distinct fall bearing red raspberry plant known as 'Marcianna' as described herein, illustrated and identified by the characteristics set forth above.

* * * * *